United States Patent [19]

Cosmescu

[11] Patent Number: 5,108,389
[45] Date of Patent: Apr. 28, 1992

[54] AUTOMATIC SMOKE EVACUATOR ACTIVATOR SYSTEM FOR A SURGICAL LASER APPARATUS AND METHOD THEREFOR

[76] Inventor: Ioan Cosmescu, 14449 N. 22nd St., Phoenix, Ariz. 85022

[21] Appl. No.: 527,589

[22] Filed: May 23, 1990

[51] Int. Cl.⁵ ............................................. A61B 17/36
[52] U.S. Cl. ....................................... 606/10; 604/35; 128/908; 200/86.5
[58] Field of Search ........................... 604/21, 23–28, 604/30, 35; 128/747, 908; 606/2, 10–12; 200/86.5; 433/101

[56] References Cited

U.S. PATENT DOCUMENTS

| | | | |
|---|---|---|---|
| 3,742,947 | 7/1973 | Hashem | 128/908 |
| 4,715,372 | 12/1987 | Philippbar et al. | 606/2 |
| 4,735,603 | 4/1988 | Goodson et al. | 604/28 |
| 4,850,352 | 7/1989 | Johnson | 604/35 |
| 4,853,772 | 8/1989 | Kikuchi | 128/908 |
| 4,983,901 | 1/1991 | Lehmer | 604/65 |

*Primary Examiner*—Stephen C. Pellegrino
*Assistant Examiner*—Ralph A. Lewis
*Attorney, Agent, or Firm*—Harry M. Weiss

[57] ABSTRACT

An automatic smoke evacuator activator system and method are disclosed preferably for use with a laser surgical apparatus which utilizes a smoke evacuator system for removing smoke and toxic fumes from the area serviced by the smoke evacuator system and a switch coupled to the laser surgical apparatus for turning on the laser cutting beam of the laser surgical apparatus and to the smoke evacuator system for simultaneously turning on the smoke evacuator system when the laser cutting beam of the laser surgical apparatus is turned on. Other features include the switch having a switch position to turn off the smoke evacuator system and the laser cutting beam of the laser surgical apparatus. A time delay is coupled to the switch for time delaying the turning off of the smoke evacuator system. In one embodiment, a transmitter and a receiver are used to control the operation of the swtich by using an infrared beam between the transmitter and receiver that is acted upon by the switch.

16 Claims, 1 Drawing Sheet 5,108,389

AUTOMATIC SMOKE EVACUATOR ACTIVATOR SYSTEM FOR A SURGICAL LASER APPARATUS AND METHOD THEREFOR

BACKGROUND OF THE INVENTION

1. Field of the Invention

This invention generally relates to smoke evacuator systems and methods therefor and, in particular, to an automatic smoke evacuator activator system for a surgical laser apparatus and method therefor which is designed such that the smoke evacuator is automatically activated when the laser cutting beam of a surgical laser apparatus is turned on and automatically deactivated, at a selected period in time, after the laser cutting beam of the surgical laser apparatus is turned off.

2. Description of the Prior Art

In the past, a surgical laser apparatus utilized a smoke evacuator system which was manually turned on and off, but was generally continuously operating during a surgical laser procedure. A smoke evacuator system functioned as part of a surgical laser apparatus. The smoke evacuator systems of many surgical laser apparatus produced a constant noise during its use or operation, used a high amount of electrical energy, and the continuous air pressure on the filter element of the smoke evacuator systems of the surgical laser apparatus usually saturated or overloaded the system's filter element and thereby allowed the toxic fumes which were supposed to be evacuated from the surgical area to escape uncontrolled into the medical operating room rather than being vented outside which was supposed to be the function of the smoke evacuator system.

Therefore, it would be a great benefit to the surgeon and operating room staff if the smoke evacuator system of the surgical laser apparatus was only activated during the time the laser cutting beam of the surgical laser apparatus was in use. For safety purposes, the FDA does not allow any device to be in electrical contact with the control circuitry of the surgical laser. For this reason, normally the smoke evacuator system of the laser surgical apparatus was manually switched on at the beginning of the surgical procedure, left on during the entire surgical procedure and then switched off at the conclusion thereof. However, the critical time period for the use of the smoke evacuator system of the laser surgical apparatus was during the period of time that the laser cutting beam of the laser surgical apparatus was in operation. Therefore, a need existed for a smoke evacuator system of a laser surgical apparatus which would sense and turn on at the initiation or start of the laser cutting beam function of the surgical laser apparatus and then turn off shortly after termination of the laser cutting beam function so that the smoke evacuation system would be limited in its function and operation to the most critical time period for the function of the laser surgical apparatus and thereby automatically operated in response to the production of smoke that would be generated by the laser cutting beam of the laser surgical apparatus.

SUMMARY OF THE INVENTION

One object of this invention is to provide an improved smoke evacuator system and method for a laser surgical apparatus.

Another object of the subject invention is to provide a smoke evacuator system and method for a laser surgical apparatus which has an automatic control that activates the smoke evacuator system only during the approximate period of time when the laser surgical apparatus is being utilized for surgical procedures which is when the laser cutting beam of the laser surgical apparatus is on.

Still another object of the subject invention is to provide a smoke evacuator system and method for a laser surgical apparatus which has delay circuitry or means to allow the continued operation of the smoke evacuator system of the surgical laser system for a variable time period (which is operator selected) after the laser cutting beam of the surgical laser apparatus has been turned off in order to remove all of the toxic smoke from the operating room prior to the turn off of the smoke evacuator system.

These and other objects, features and advantages of the present invention, as well as details of the preferred embodiment thereof, will be more fully understood from the following description and drawing.

DESCRIPTION OF THE PREFERRED EMBODIMENTS

Figure 1:
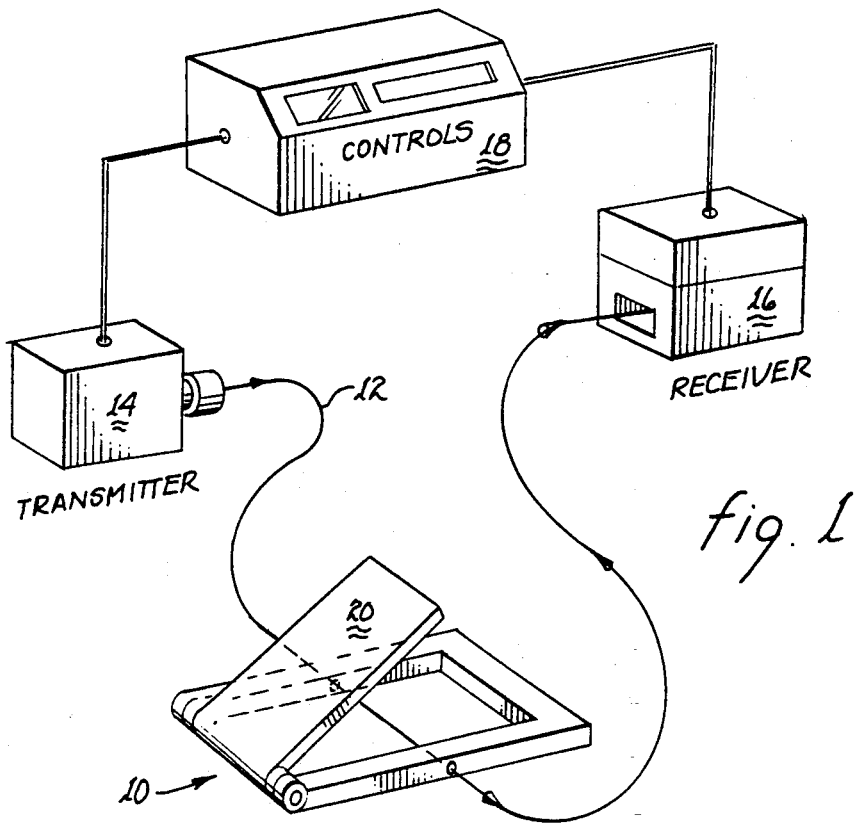
FIG. 1 is a perspective view, of a control system in accordance with this invention in combination with a foot switch that is coupled to a surgical laser apparatus (not shown) that is used for turning on the laser cutting bean of the laser cutting apparatus.

In accordance with one embodiment of this invention, an automatic smoke evacuator activator system for a laser surgical apparatus is provided which comprises transmitter means for generating and transmitting a beam of electromagnetic radiation; receiver means coupled to the transmitter means for receiving the beam of electromagnetic radiation; switch means located between the transmitter means and the receiver means for operating on the beam of electromagnetic radiation to cause the receiver means to generate an electronic signal; and smoke evacuator system means coupled to the receiver means for receiving the electronic signal from the receiver means to activate the smoke evacuator system means to remove undesired smoke and toxic fumes from the area serviced by the smoke evacuator system means. Preferably, the beam of electromagnetic radiation is a beam of infrared radiation switch means is preferably a foot switch electrically coupled to the laser surgical apparatus. The foot switch has means for interrupting the beam of electromagnetic radiation and the receiver means functions to generate the electronic signal to activate the smoke evacuator system means when the beam of electromagnetic radiation is interrupted by the foot switch. The receiver means turns off the smoke evacuator system means when the beam of electromagnetic radiation is received by the transmitter means after the foot switch is released. Time delay means are coupled to the receiver means for time delaying the turning off of the smoke evacuator system means.

In accordance with another embodiment of this invention an automatic smoke evacuator activator system is provided for a laser surgical apparatus which comprises smoke evacuator system means for removing smoke and toxic fumes from the area serviced by the smoke evacuator system means; and switch means coupled to both the laser surgical apparatus for turning on the laser cutting beam of the laser surgical apparatus and to the smoke evacuator system means for simultaneously turning on the smoke evacuator system means when the laser cutting beam of the laser surgical apparatus is turned on. The switch means has a position to turn off the smoke evacuator system means and the laser cutting beam of the laser surgical apparatus. Time delay means as coupled to the switch means for time delaying off of said smoke evacuator system means. In accordance with still another embodiment medical laser system is provided which comprises of this invention, a laser surgical apparatus; smoke evacuator system means for removing smoke and toxic fumes from the area adjacent to the laser surgical apparatus; and switch means coupled to (a) the laser surgical apparatus for turning on the laser cutting beam of the laser surgical apparatus and (b) the smoke evacuator system means for simultaneously turning on the smoke evacuator system means when the laser cutting beam of the laser surgical apparatus is turned on. The switch means has a switch position to turn off the smoke evacuator system means and the laser cutting beam of the laser surgical apparatus. Time delay means are coupled to the switch means for time delaying the turning off of the smoke evacuator system means.

In accordance with a further embodiment of this invention, a method is provided for an automatic smoke evacuator activator system for a laser surgical apparatus. The method comprises the steps of:

Providing transmitter means for generating and transmitting a beam of electromagnetic radiation; providing receiver means coupled to the transmitter means for receiving the beam of electromagnetic radiation; interposing switch means between the transmitter means and the receiver means for operating on the beam of electromagnetic radiation to cause the receiver means to generate an electronic signal; and coupling smoke evacuator system means to the receiver means for receiving the electronic signal from the receiver means to activate the smoke evacuator system means to remove undesired smoke and toxic fumes from the area serviced by the smoke evacuator system means. The beam of electromagnetic radiation is a beam of infrared radiation. The switch means is a foot switch electrically coupled to the laser surgical apparatus. The foot switch has means for interrupting the beam of electromagnetic radiation and the receiver means generates the electronic signal to activate the smoke evacuator system means when the beam of electromagnetic radiation is interrupted by the foot switch. The receiver means turns off said smoke evacuator system means when said beam of electromagnetic radiation is received by said transmitter means after said foot switch is released. Time delay means are coupled to the receiver means for time delaying the turning off of the smoke evacuator system means.

In accordance with still another embodiment of this invention, a method is provided for an automatic smoke evacuator activator system for a laser surgical apparatus which comprises the steps of providing smoke evacuator system means for removing smoke and toxic fumes from the area serviced by the smoke evacuator system means; and coupling switch means to both the laser surgical apparatus for turning on the laser cutting beam of the laser surgical apparatus and to the smoke evacuator system means for simultaneously turning on the smoke evacuator system means when the laser cutting beam of the laser surgical apparatus is turned on. The switch means has a switch position to turn off the smoke evacuator system means and the laser cutting beam of the laser surgical apparatus. Time delay means are coupled to the switch means for time delaying off of said smoke evacuator system means.

In accordance with a still further embodiment of this invention, a method is provided for a medical laser system which comprises the steps of: smoke evacuator system means for removing smoke and toxic fumes from the area adjacent to the laser surgical apparatus; and coupling switch means to (a) the laser surgical apparatus for turning on the laser cutting beam of the laser surgical apparatus and (b) the smoke evacuator system means for simultaneously turning on the smoke evacuator system means when the laser cutting beam of the laser surgical apparatus is turned on. The switch means has a switch position to turn off the smoke evacuator system means and the laser cutting beam of the laser surgical apparatus. Time delay means are coupled the switch means for time delaying the turning off of the smoke evacuator system means.

DESCRIPTION OF THE SPECIFICATION

Referring to FIG. 1, in this embodiment of the invention, the activation unit to serve as the automatic activator for the smoke evacuator system (see FIG. 2) of a surgical laser system (see FIG. 2) is foot switch assembly 10. The foot switch assembly 10 is located in such a way that, for example, an electromagnetic radiation beam such as an infrared beam 12 generated by a transmitter 14 preferably passes from one side of the foot switch assembly 10 to be sensed by a receiver 16 located on the other side of the foot switch assembly 10. The transmitter 14 is preferably any suitable infrared beam generating transmitter whereas the receiver 16 is preferably any suitable infrared beam sensing receiver. Controls 18 are electrically coupled to both the transmitter 14 and the receiver 16 to provide electrical control for turning on the transmitter 14, turning on the receiver 16, controlling the power applied to both the transmitter 14 and the receiver 16, turning off either or both the transmitter 14 and the receiver 16, etc.

As can be seen by reference to FIG. 1, depressing foot contact member 20 of the foot switch assembly 10 causes the foot contact member 20 to pivot downwardly and thereby cut-off or interrupt the infrared beam 12 going from the transmitter 14 to the receiver 16. In actual practice, the foot switch assembly 10 is located between the output beam transmitting portion of the transmitter 14 and the input beam receiving portion of the receiver 16. Thus, there would be a straight line beam between the transmitter 14 and the receiver 16 (not as shown in FIG. 1 which is illustrated in the manner shown merely for ease in seeing and understanding the operation of the foot switch assembly 10 with respect to the transmitter 14 and the receiver 16). Thus, aligned openings in, for example, the bottom portion of the foot switch assembly 10 permit the infrared beam 12 to pass through the foot switch assembly 10 when it is in its normally off position which is when the foot contact member 20 is in its raised position as shown in FIG. 1. Therefore, in this normally off position (as shown in FIG. 1) the infrared beam passes from the transmitted 14 to the receiver 16. However, when the foot contact member 20 (which is preferably spring biased upwardly to its normally off position as shown in FIG. 1) is depressed by the action of the foot of an operator, the infrared beam 12 is interrupted or blocked because of the beam blocking action of the foot contact member 20. The interrupting of the infrared beam 12 by the action of the foot contact member 20 is sensed by the receiver 16 which is electronically configured to sense the absence of the receipt of the infrared beam 12 from the transmitter 14. The interruption of the beam 12 causes the receiver 16 to generate an electronic signal (see FIG. 2) which is used to activate both a laser surgical apparatus 30 and a smoke evacuator 32.

Figure 2:
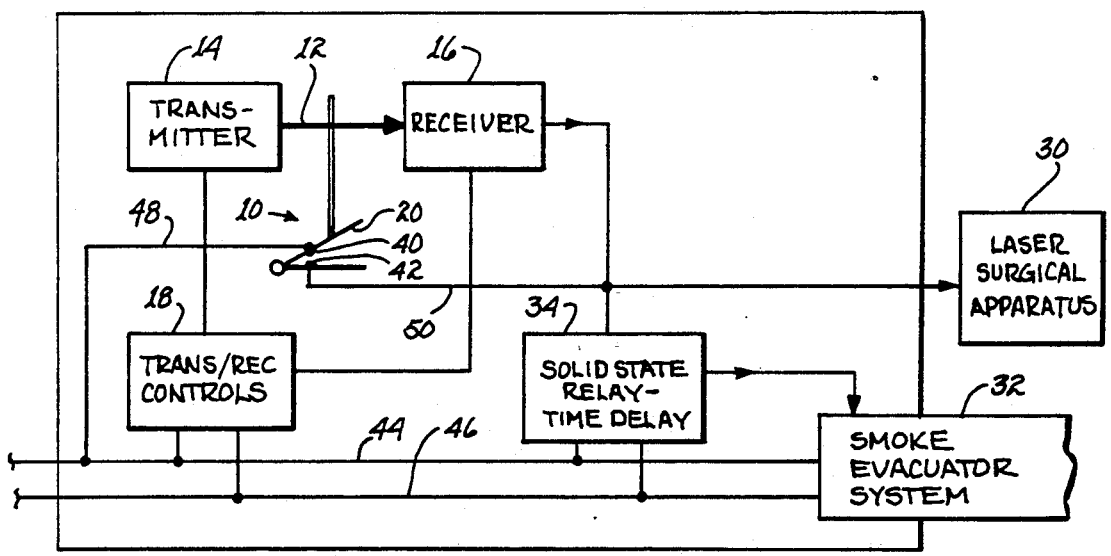
FIG. 2 is an electronic block diagram view of the control system of FIG. 1 as it is used to operate the smoke evacuator system that is coupled to a surgical laser apparatus (not shown).

Referring more specifically to FIG. 2, the laser surgical apparatus utilizes a, for example, Carbon Dioxide ($CO_2$) high energy gas laser (not shown) for generating a laser cutting beam to perform a surgical function. The laser cutting beam of the surgical laser apparatus 30 is activated by depressing the foot control member 20 of the foot switch assembly 10 depicted in both FIGS. 1 and 2. When the laser cutting beam of the surgical laser apparatus 30 is activated by depressing the foot contact member 20 of the foot switch assembly 10 the infrared beam is broken or interrupted and an electrical signal is generated by the receiver 16 which indicates that the beam has been broken. This electronic signal from the receiver 16 is supplied to the electronic circuitry of the laser surgical apparatus 30 and the smoke evacuator system 32 to turn on, at the same time, the laser cutting beam of the laser surgical apparatus 30 and the smoke evacuator system 32. The electronic signal from the receiver 16 is supplied to the smoke evacuator system 32 by means of solid state relay 34 which cooperates with the electronic circuitry of the smoke evacuator system 32 to turn on the smoke evacuator system 32. When the laser surgeon completes the operation or surgical procedure, the surgeon turns of the laser cutting beam of the laser surgical apparatus 30 by releasing foot contact member 20 of the foot switch assembly 10, and the infrared beam is again allowed to pass between the transmitter 14 and there receiver 16. The sensing of the infrared beam by the receiver 16 causes the receiver 16 to turn off the electronic signal that was generated at the output of the receiver 16 when the foot contact member 20 was in its down (activated) position. Thus, either the absence of this electronic signal at the output of the receiver 16 or, if desired, the generation of a different electronic signal at the output of the receiver 16, when the infrared beam is sensed by the receiver 16, causes shut off of the laser cutting beam, the laser surgical apparatus 30 and, at the same time, provides an indication in the solid state relay (and time delay) 34 that the foot switch assembly 10 is in its off position. A manually adjustable timer (not shown) which is included as part of the circuitry of the solid state relay-time delay box 34 sets the time delay of the operation of the solid state relay that is used to turn off the smoke evacuator system 32 thereby continuing the operation of the smoke evacuator system 32 for a variable period of time (as determined by the adjustable timer) after the laser cutting beam of the laser surgical apparatus 30 is turned off. For example, a time delay of a few seconds would be desirable. Therefore, the smoke evacuator system 32 can be turned off a short time after the turning off of the laser surgical apparatus 38 thereby cleaning the air in the surgery area of toxic fumes and smoke.

While the invention has been particularly shown and described with reference to a preferred embodiment thereof, it will be understood by those skilled in the art that changes in form and detail may be made therein without departing from the spirit and the scope of the invention.

The embodiment depicted in FIG. 2 conceptualizes the action of the foot switch assembly 10 with the foot contact member 20 to break or interrupt the beam 12 when the foot contact member 20 (as shown in FIG. 1) is depressed.

Alternatively, if desired, the transmitter 14 and the receiver 16 can be replaced or enhanced by the action (or the back up action) of micro-switches 40 and 42 associated with the foot switch assembly 10. Thus, depressing the foot contact member 20 serves to electrically connect microswitch (or electrical contact) 40 with the microswitch (or electrical contact) 42 thereby closing the circuit from a power supply (not shown) that is connected to parallel lines 44 and 46. Therefore, when the circuit is closed, an electrical signal from the power supply (not shown) is transmitted via conductor 48, microswitch or contact 40, microswitch or contact 42, and conductor 50 to both the circuit to turn on the laser cutting beam of the laser surgical apparatus 30 and, via the solid state relay-time delay box, the smoke evacuator system 32 thereby turning it on also. When the foot contact member 20 is elevated, the electrical circuit comprising the power supply (not shown), conductor 48, microswitches or contacts 40 and 42, and conductor 50 is opened up because of the gap between the microswitches or contacts 40 and 42. The lack of a signal to the laser surgical apparatus 30 and the solid state relay-time delay box 34 because of this open circuit condition causes immediate shut off of the laser cutting beam of the laser surgical apparatus 30 as well as to cause, due to the action of the time delay function of the box 34, subsequent turn off a short time later of the smoke evacuator system 32.

While the invention has been particularly shown and described with reference to a preferred embodiment thereof, it will be understood by those skilled in the art that changes in form and detail may be made therein without departing from the spirit and the scope of the invention. For example, instead of a smoke evacuator system being turned on and off as shown in the drawings, another unit can be similarly turned on and off in conjunction with the laser surgical apparatus.

I claim:

1. An automatic smoke evacuator activator system for a laser surgical apparatus comprising, in combination,
   transmitter means for generating and transmitting a beam of electromagnetic radiation;
   receiver means coupled to said transmitter means for receiving said beam of electromagnetic radiation;
   switch means located between said transmitter means and said receiver means for operating on said beam of electromagnetic radiation to cause said receiver means to generate an electronic signal; and
   smoke evacuator system means coupled to said receiver means for receiving said electronic signal from said receiver means to activate said smoke evacuator system means to remove undesired smoke and toxic fumes from the area serviced by said smoke evacuator system means.

2. The system of claim wherein said beam of electromagnetic radiation further comprise a beam of infrared radiation.

3. The system of claim 1 wherein said switch means further comprises: means making said switch means foot operated; and electrical contact means mechanically coupled to said switch means and electrically coupled to said laser surgical apparatus for producing an electrical signal for controlling a function of said laser surgical apparatus when said switch means operates on said beam of electromagnetic radiation.

4. The system of claim 3 wherein said foot switch further comprises means for interrupting said beam of electromagnetic radiation, said receiver means generating said electronic signal to activate said smoke evacuator system means when said beam of electromagnetic radiation is interrupted by said foot switch.

5. The system of claim 4 wherein said receiver means ceases to generate said electronic signal at the time said beam of electromagnetic radiation is received by said receiver means after said foot switch is released so that said smoke evacuator means is turned off at said time.

6. The system of claim 4 wherein said receiver means ceases to generate said electronic signal at the time said beam of electromagnetic radiation is received by said receiver means after said foot switch is released, and further comprising time delay means for defining an interval of time, said time delay means coupled to said receiver means so that said smoke evacuator system means is turned off after said interval of time after said time said beam of electromagnetic radiation is received by said receiver means after said foot switch is released.

7. An automatic smoke evacuator activator system for a laser surgical apparatus comprising, in combination,
smoke evacuator system means for removing smoke and toxic fumes from the area serviced by said smoke evacuator system means; and
switch means which is adapted to be coupled to said laser surgical apparatus for turning on the laser cutting beam of the laser surgical apparatus and which is coupled to said smoke evacuator system means for simultaneously turning on said smoke evacuator system means when the laser cutting beam of said laser surgical apparatus is turned on;
said switch means further comprising a switch position to turn off said smoke evacuator system means and the laser cutting beam of the laser surgical apparatus and time delay means coupled to said switch means for time delaying said turn off of said smoke evacuator means.

8. A medical laser system comprising, in combination, a laser surgical apparatus;
smoke evacuator system means for removing smoke and toxic fumes from the area adjacent to said laser surgical apparatus; and
switch means coupled to (a) said laser surgical apparatus for turning on the laser cutting beam of said laser surgical apparatus and (b) said smoke evacuator system means for simultaneously turning on said smoke evacuator system means when the laser cutting beam of said laser surgical apparatus is turned on;
said switch means further comprising a switch position to turn off said smoke evacuator system means and to turn off the laser cutting beam of said laser surgical apparatus; and
time delay means coupled to said switch means for delaying the time of the turning off of said smoke evacuator system with respect to the time of the turning off of said laser cutting beam of said laser surgical apparatus.

9. A method for providing an automatic smoke evacuator activator system for a laser surgical apparatus comprising the steps of,
providing transmitter means for generating and transmitting a beam of electromagnetic radiation;
providing receiver means coupled to said transmitter means for receiving said beam of electromagnetic radiation;
providing switch means between said transmitter means and said receiver means for operating on said beam of electromagnetic radiation to cause said receiver means to generate an electronic signal; and
coupling smoke evacuator system means to said receiver means for receiving said electronic signal from said receiver means to activate said smoke evacuator system means to remove undesired smoke and toxic fumes from the area serviced by said smoke evacuator system means.

10. The method of claim 9 wherein said beam of electromagnetic radiation further comprises a beam of infrared radiation.

11. The method of claim 9 wherein said switch means further comprises a foot switch adapted to be coupled electrically to said laser surgical apparatus.

12. The method of claim 11 wherein said foot switch comprising means for interrupting said beam of electromagnetic radiation, said receiver means generating said electronic signal to activate said smoke evacuator system means when said beam of electromagnetic radiation is interrupted by said foot switch.

13. The method of claim 12 wherein said receiver means ceases to generate said electronic signal at the time said beam of electromagnetic radiation is received by said receiver means after said foot switch is released so that said smoke evacuator means is turned off at said time.

14. The method of claim 12 wherein said receiver means ceases to generate said electronic signal at the time said beam of electromagnetic radiation is received by said receiver means after said foot switch is released and further comprising time delay means for defining an interval of time, said time delay means coupled to said receiver means so that said smoke evacuator system means is turned off after said interval of time after said time said beam of electromagnetic radiation is received by said receiver mean after said foot switch is released.

15. A method for providing an automatic smoke evacuator activator system for a laser surgical apparatus comprising the step of:
providing smoke evacuator system means for receiving smoke and toxic fumes from the area serviced by said smoke evacuator system means; and
coupling switch means is adapted to be coupled to said laser surgical apparatus for turning on the laser cutting beam of the laser surgical apparatus and which is coupled to said smoke evacuator system means for simultaneously turning on said smoke evacuator system means when the laser cutting beam of said laser surgical apparatus is turned on;
said switch means having a switch position to turn off said smoke evacuator system means and the laser cutting beam of said laser surgical apparatus and time delay means coupled to said switch means for time delaying said turn off of said smoke evacuator means.

16. A method for providing a medical laser system comprising the steps of:

providing a laser surgical apparatus;
providing smoke evacuator system means for removing smoke and toxic fumes from the area adjacent to said laser surgical apparatus; and
providing switch means coupled to (a) said laser surgical apparatus for turning on the laser cutting beam of said laser surgical apparatus and (b) said smoke evacuator system means for simultaneously turning on said smoke evacuator system means when the laser cutting beam of said laser surgical apparatus is turned on;
said switch means further comprising a switch position to turn off said smoke evacuator system means and to turn off the laser cutting beam of said laser surgical apparatus; and
time delay means coupled to said switch means for delaying the time of the turning off of said smoke evacuator system with respect to the time of the turning off of said laser cutting beam of said laser surgical apparatus.

* * * * *

UNITED STATES PATENT AND TRADEMARK OFFICE
CERTIFICATE OF CORRECTION

PATENT NO. : 5,108,389
DATED : 4-28-92
INVENTOR(S) : Ioan Cosmescu

It is certified that error appears in the above-identified patent and that said Letters Patent is hereby corrected as shown below:

IN THE CLAIMS:

Claim 2, line 1, after "claim" insert -- 1 --.

Claim 14, line 10, change "mean" to -- means --.

Claim 15, line 3, change "step" to -- steps -- .

lines 4 and 5, change "receiving" to -- removing --.

Signed and Sealed this

Twenty-ninth Day of June, 1993

Attest:

MICHAEL K. KIRK

Attesting Officer      Acting Commissioner of Patents and Trademarks